United States Patent
Bocian

(10) Patent No.: US 10,881,627 B1
(45) Date of Patent: *Jan. 5, 2021

(54) NON-SURGICAL LASER TREATMENT FOR A FIBROUS MASS

(71) Applicant: BBBN, PLLC, Tucson, AZ (US)

(72) Inventor: Darin Bocian, Tucson, AZ (US)

( * ) Notice: Subject to any disclaimer, the term of this patent is extended or adjusted under 35 U.S.C. 154(b) by 11 days.

This patent is subject to a terminal disclaimer.

(21) Appl. No.: 16/358,596

(22) Filed: Mar. 19, 2019

Related U.S. Application Data

(62) Division of application No. 15/225,402, filed on Aug. 1, 2016, now Pat. No. 10,231,942.

(60) Provisional application No. 62/297,693, filed on Feb. 19, 2016, provisional application No. 62/198,787, filed on Jul. 30, 2015.

(51) Int. Cl.
| | |
|---|---|
| A61N 5/06 | (2006.01) |
| A61K 31/192 | (2006.01) |
| A61K 31/522 | (2006.01) |
| A61B 5/055 | (2006.01) |
| A61K 31/277 | (2006.01) |
| A61B 5/00 | (2006.01) |
| A61B 8/08 | (2006.01) |
| A61N 5/067 | (2006.01) |

(52) U.S. Cl.
CPC ............ A61K 31/192 (2013.01); A61B 5/055 (2013.01); A61K 31/277 (2013.01); A61K 31/522 (2013.01); A61N 5/0613 (2013.01); A61B 5/4041 (2013.01); A61B 8/085 (2013.01); A61N 5/0622 (2013.01); A61N 2005/067 (2013.01)

(58) Field of Classification Search
CPC ....... A61B 5/055; A61B 5/4041; A61B 8/085; A61K 31/192; A61K 31/277; A61K 31/522; A61N 5/0613; A61N 5/0622; A61N 2005/067

See application file for complete search history.

(56) References Cited

U.S. PATENT DOCUMENTS

| | | | |
|---|---|---|---|
| 7,883,534 B1 | 2/2011 | Crosby | |
| 10,231,942 B2 * | 3/2019 | Bocian | A61K 31/192 |
| 2006/0129022 A1 | 6/2006 | Venza | |
| 2007/0213792 A1 * | 9/2007 | Yaroslavsky | A61N 5/0613 607/100 |
| 2007/0219605 A1 * | 9/2007 | Yaroslavsky | A61N 5/0613 607/100 |
| 2011/0105996 A1 | 5/2011 | Mustoe | |
| 2013/0310905 A1 | 11/2013 | Crosby | |
| 2014/0343542 A1 | 11/2014 | Karnik | |

OTHER PUBLICATIONS

Lana H. Gimber et al., Ultrasound Evaluation of Morton Neuroma Before and After Laser Therapy, American Journal of Roentgenology, Feb. 2017, 208:2, pp. 380-385.

* cited by examiner

*Primary Examiner* — Eric D. Bertram
(74) *Attorney, Agent, or Firm* — Greenberg Traurig, LLP

(57) ABSTRACT

Systems and methods for treating a fibrous mass, which is comprised of a plantar fibroma, are disclosed. In one exemplary implementation, a method may comprise identifying a location of the fibrous mass and non-surgically delivering electromagnetic energy to the fibrous mass. Embodiments may include delivering the energy via a Nd:Yag laser at various specified parameters, such as energy level, pulse count, and tissue depth, among others.

24 Claims, 6 Drawing Sheets

NON-SURGICAL LASER TREATMENT FOR A FIBROUS MASS

CROSS-REFERENCE TO RELATED APPLICATIONS

This is a division of application Ser. No. 15/225,402, filed Aug. 1, 2016, published as US2017/0028217A1, now U.S. Pat. No. 10,231,942, which claims benefit/priority of U.S. provisional application No. 62/198,787, filed on Jul. 30, 2015, and of U.S. provisional application No. 62/297,693, filed on Feb. 19, 2016, all of which are incorporated herein by reference in entirety.

FIELD

This invention relates to a non-surgical treatment for a fibrous mass, such as Morton's neuroma and plantar fibroma.

BACKGROUND

Perineural fibrosis with axonal degeneration and vascular proliferation of the common digital nerve of the second or third intermetatarsal space are often referred to as a Morton's neuroma. It is believed that fibrosis along with degeneration of the nerve occurs as a result of mechanical irritation or entrapment between the adjacent metatarsal heads. Pain, tingling and numbness are the most common symptoms. Pain can progress to lifestyle limiting.

Referring now to FIG. 1, Morton's neuroma (also known as Morton neuroma, Morton's metatarsalgia, Morton's neuralgia, plantar neuroma, intermetatarsal neuroma, and interdigital neuroma) is a benign neuroma of an intermetatarsal plantar nerve, most commonly of the second and third intermetatarsal spaces (between 2nd-3rd and 3rd-4th metatarsal heads).

Prior art treatment has included shoe modification, use of orthotic devices, corticosteroid injections, alcohol sclerosing injections, and surgical neurectomy.

A fibroma is a non-cancerous, i.e., benign, fibrous tissue tumor or growth, that can occur anywhere in the body. For example, on the plantar, or the bottom surface of the foot, the fibromas are called plantar fibromas. Unlike plantar warts, which grow on the skin, plantar fibromas grow within the plantar fascia, which is a thickened, fibrous sheet of connective tissue that originates from the plantar aspect of medial tubercle of the calcaneus and extends to the plantar plates of the metatarsophalangeal joints with a function of absorbing shock for the foot during ambulation. The plantar fascia is one of the most important ligamentous bands that maintain the longitudinal arch of the foot.

The etiology of plantar fibromas have not been clearly identified, but it is more than likely multifactorial. The typical etiology is repetitive stress overload to the origin of the plantar fascia, together with other causes, such as weight gain, excessive pronation, occupation-related activity, anatomical variations, altered biomechanics (i.e., gait abnormalities), overexertion, and inadequate foot wear.

Plantar fibromas can develop in one or both feet and the common growth is usually a solitary nodule, though multiple nodules are possible in the same foot. The mid-arch region of the foot is the most common location for planter fibromas to develop. However, plantar fibromas can appear anywhere along the underside of the foot. They can occur in people of any age and gender and will not resolve on their own or become smaller without proper treatment.

Prior art treatment can be divided into conservative and surgical measures. Conservative and prior art non-surgical measures can alleviate the pain of a plantar fibroma, but they will not reduce the mass or prevent the progression of the plantar fibroma. These measures typically include steroid injections, orthotic devices (i.e., orthopedic shoe insoles), anti-inflammatory drugs, and physical therapy. Operative measures are needed when the above measures fail to improve symptoms of the plantar fibroma. However, surgical removal of the plantar fibroma requires outpatient care and may result in a flattening of the arch or development of hammertoes. Recurrence of the plantar fibroma occurs even after surgical measures.

SUMMARY

Embodiments of applicant's disclosure describe a method for treating a fibrous mass, which comprises a Morton's neuroma or a plantar fibroma. The method comprises identifying a location of the fibrous mass, determining a first size of the fibrous mass, non-surgically delivering electromagnetic energy to the fibrous mass, and determining a second size of the fibrous mass. The method further comprises determining a number of a plurality of treatments. In some embodiments, when treating the Morton's neuroma, the method further comprising manipulating the Morton's neuroma into a position adjacent a surface of the patient's foot.

In certain embodiments, medical imaging techniques, such as ultrasound imaging and magnetic resonance imaging, are used to identify the location of the fibrous mass and to determine the first size of the fibrous mass. In other embodiments, identifying the location of the fibrous mass further includes placing a patient in a supine position, palpating the patient's skin over a suspected location of the fibrous mass, and detecting an audible click when palpating skin directly over the fibrous mass.

In certain embodiments, the delivering electromagnetic energy to the fibrous mass step further comprises emitting electromagnetic energy from a lasing device in about a 5 mm diameter beam, adjusting a power of to the lasing device such that the electromagnetic energy penetrates tissues to a depth of about 6 mm to about 8 mm, directing the 5 mm beam onto the location for a length of time between about 10 minutes to about 15 minutes, and delivering about 1,000 pulses of the 5 mm beam to the location. In some embodiments, a Nd:YAG lasing device can be utilized.

In certain embodiments, a topical medication is applied directly on the skin of the location of the fibrous mass. The topical medication is selected from a group consisting of cream, gel, ointment, and lotion. In some embodiments, the applying the topical medication step further comprises using about 15% verapamil by weight, about 3% pentoxifylline by weight, and about 1% tranilast by weight. In other embodiments, the applying the topical medication step further comprises using about 15% verapamil by volume, about 3% pentoxifylline by volume, and about 1% tranilast by volume.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
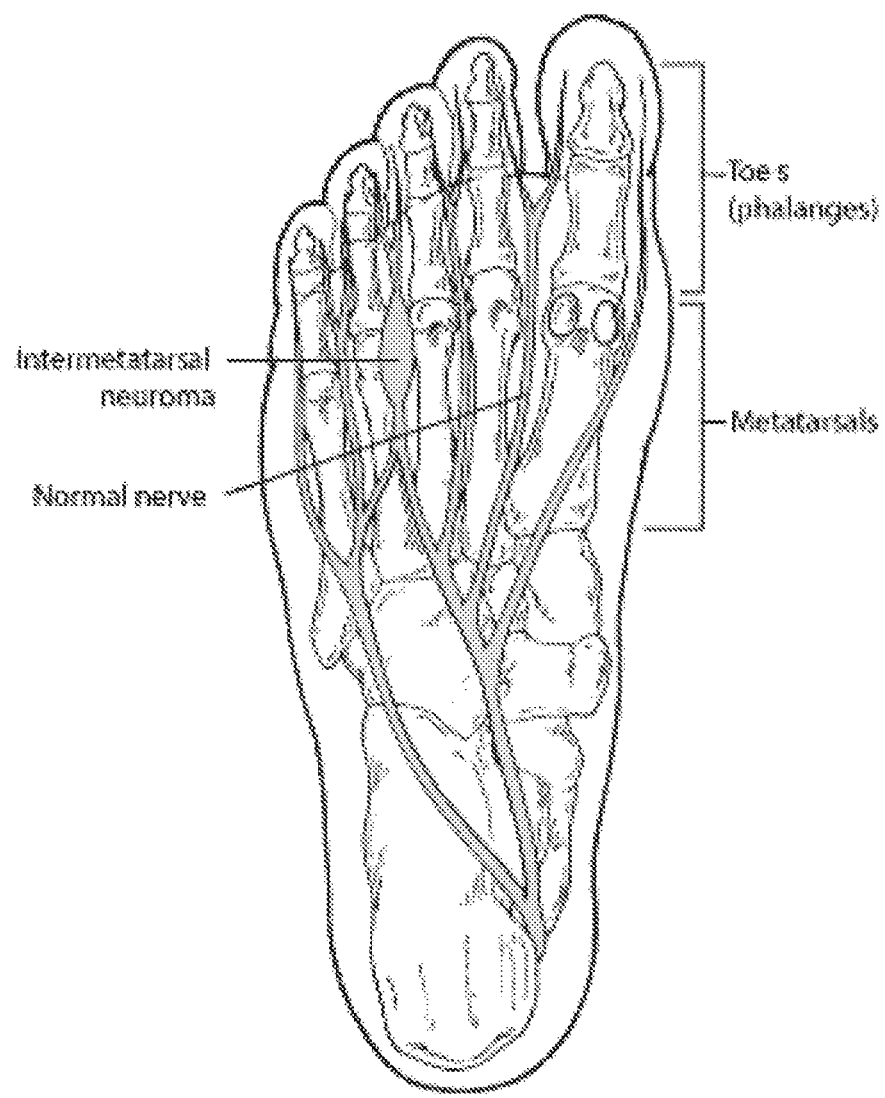
FIG. 1 illustrates the anatomy of the medial plantar nerve and the lateral plantar nerve.

Referring now to FIG. 1, perineural fibrosis of the common digital nerve of the second or third intermetatarsal space is often referred to as a Morton's neuroma. It is believed that fibrosis along with degeneration of the nerve occurs as a result of mechanical irritation or entrapment between the adjacent metatarsal heads. Pain, tingling and numbness are the most common symptoms. Pain can progress to lifestyle limiting.

Applicant has found that Morton's neuroma can be effectively treated using non-surgical treatments of laser energy. Surgery is a technology consisting of a physical intervention on tissues, and muscle. As a general rule, a procedure is considered surgical when it involves cutting of a patient's tissues or closure of a previously sustained wound. Applicant's method to treat Morton's neuroma neither involves cutting of a patient's tissues, nor closure of a previously sustained wound.

Other procedures, such as angioplasty or endoscopy, may be considered surgery if they involve "common" surgical procedure or settings, such as use of a sterile environment, anesthesia, antiseptic conditions, typical surgical instruments, and suturing or stapling. Applicant's method to treat Morton's neuroma does not require a sterile environment, anesthesia, antiseptic conditions, surgical instruments, suturing, or stapling.

Figure 2:
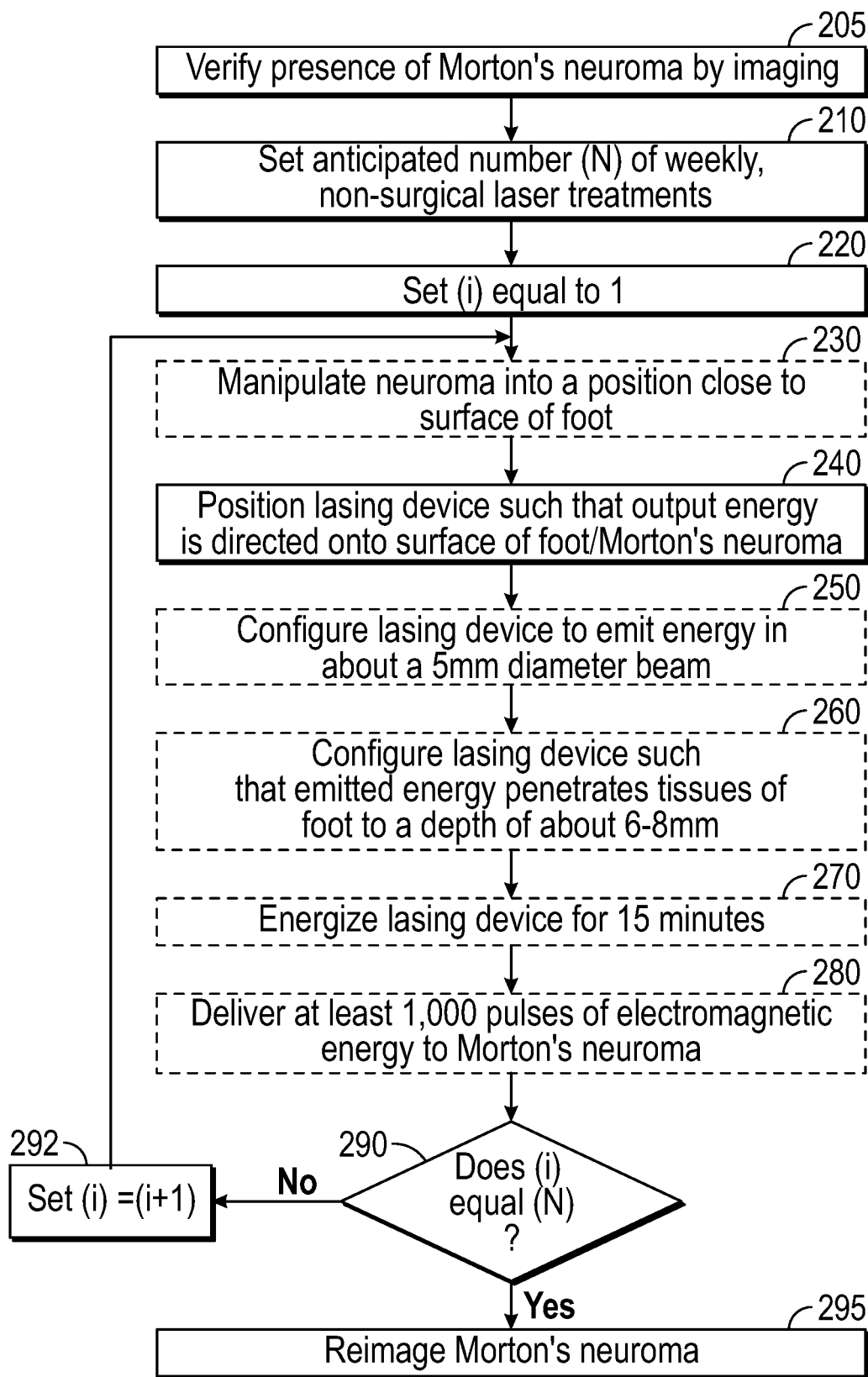
FIG. 2 is a flowchart summarizing the steps of Applicant's method for treating Morton's neuroma.

FIG. 2 summarizes the steps of Applicant's method for treating Morton's neuroma. Referring now to FIG. 2, in step 205 the method verifies the presence of a Morton's neuroma using one or more medical imaging techniques. Such medical imaging techniques include, without limitation magnetic resonance imaging ("MRI") and/or ultrasound imaging.

In certain embodiments, the target area of the neuroma is identified using Applicant's "Dull Probe Technique," wherein that technique includes using a dull probe while patient is in the supine position, palpating the intermetatarsal space to elicit pain consistent with their chief complaint and/or a positive Mulder's sign (an audible click). A diagnostic ultrasound is also used to identify the specific location of the neuroma. The target area is marked on the plantar surface of foot to guide laser treatment.

In step 210, and based upon the medical imaging of step 210, set an anticipated number of weekly, non-surgical laser treatments. In step 220, the method sets a variable (i) to 1.

In step 230, the method manipulates the verified Morton's neuroma into a position adjacent to a surface of the patient's foot. In step 240, the method positions a lasing device such that output power emitted by that lasing device is directed onto the surface of the patient's foot directly over the plantar surface of the Morton's neuroma.

In certain embodiments, step 230 further comprises applying a topical medication to the surface of the foot directly over top of the Morton's neuroma. Applicant's topical medication is made by a compounding pharmacy and comprises Verapamil 15%, Pentoxifylline 3% and Tranilast 1%. The medication is applied just prior to the laser treatment and is allowed to absorb.

Applicant's topical medication is used to treat fibrotic conditions, like plantar fibromas and Dupuytren contracture and scarring. Applicant has found that use of this topical medication assists treatment of the fibrosis around the nerve when used with the Nd:YAG laser.

In certain embodiments, the lasing device of step 240 comprises a Nd:YAG laser.

In step 250, the method configures the lasing device of step 240 to emit electromagnetic energy in a beam of a about 5 mm spot size diameter. In step 260, the method configures the lasing device such that electromagnetic energy emitted by that lasing device penetrates tissues of the foot to a depth of between 6 mm and 8 mm. Applicant has demonstrated with magnetic resonance imaging that this tissue depth is sufficient to reach the candidate nerve.

In step 270, the method energizes the lasing device for between about 10 to about 15 minutes. In step 280 in certain embodiments, the method non-surgically delivers about 1,000 pulses of electromagnetic energy at 15 J/cm, 6 msec and 7 Hz to the Morton's neuroma. Step 180 does not include cutting of the patient's skin. More specifically, step 180 does not include cutting the patient's skin disposed over or adjacent to the palpated Morton's neuroma. Step 180 does not include closure of a previously sustained wound.

In step 280 in certain embodiments, the method non-surgically delivers about 1,000 pulses of electromagnetic energy to the Morton's neuroma.

In step 290, the method determines if (i) equals (N). If the method determines in step 290, that (i) does not equal (N), then the method transitions from step 290 to step 292 wherein the method increments (i) by 1, i.e. sets (i) equal to (i+1), The method then transitions from step 292 to step 230 and continues as described herein.

If the method determines in step 290, that (i) does equal (N), then the method transitions from step 290 to step 295 wherein the method reimages the Morton's neuroma.

Figure 3:
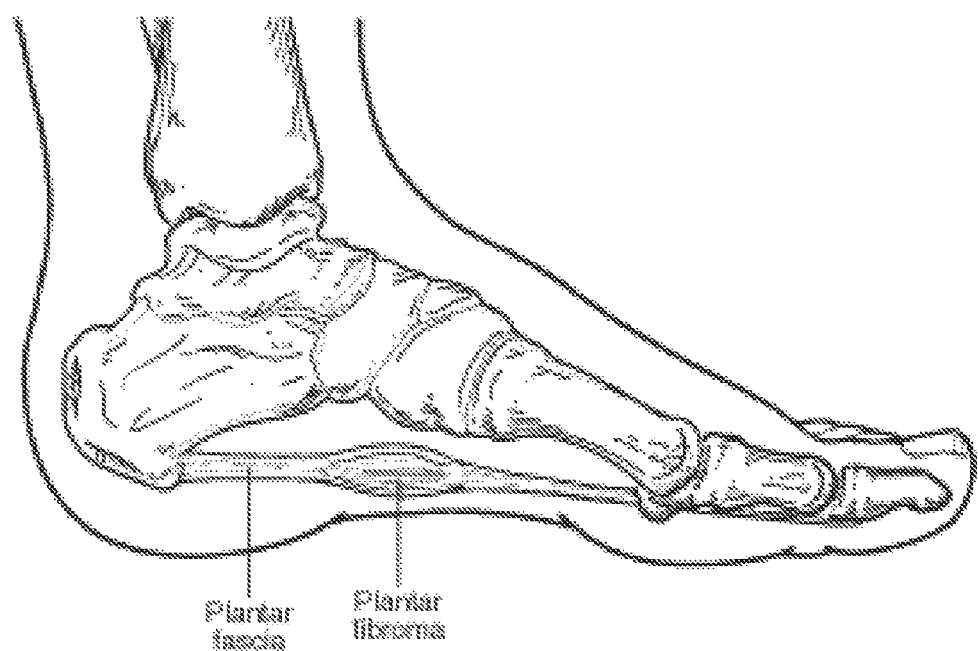
FIG. 3 illustrates the anatomy of the plantar fascia and the plantar fibroma.

Referring now to FIG. 3, a fibrous knot or nodule that is embedded within the planter fascia is often referred to as a plantar fibroma. More invasive, rapid-growing fibromas are considered plantar fibromatosis. The characteristic sign of a plantar fibroma is a noticeable lump in the arch or instep, between the heel pad and the forefoot pad. The typical plantar fibroma appears as a focal, often oval-shaped area with disorganization within the plantar fascia. Larger lesions may be lobulated and can demonstrate a central scar-like appearance with fibers radiating from the plantar fascia. The mass will cause a soft convexity in the contour of the bottom of the foot that may be painful with pressure. Also, prolonged walking and wearing shoes can cause pain or discomfort. In some cases, the mass of the plantar fibroma can progress to cause pain to limit patients' lifestyles.

Applicant has found that plantar fibromas can be effectively treated using non-surgical treatments of laser energy. Surgery is a technology consisting of a physical intervention on tissues, and muscle. As a general rule, a procedure is considered surgical when it involves cutting of a patient's tissues or closure of a previously sustained wound. Applicant's method to treat plantar fibromas neither involves cutting of a patient's tissues, nor closure of a previously sustained wound.

Other procedures, such as angioplasty or endoscopy, may be considered surgery if they involve "common" surgical procedure or settings, such as use of a sterile environment, anesthesia, antiseptic conditions, typical surgical instruments, and suturing or stapling. Applicant's method to treat plantar fibromas does not require a sterile environment, anesthesia, antiseptic conditions, surgical instruments, suturing, or stapling.

Figure 4:
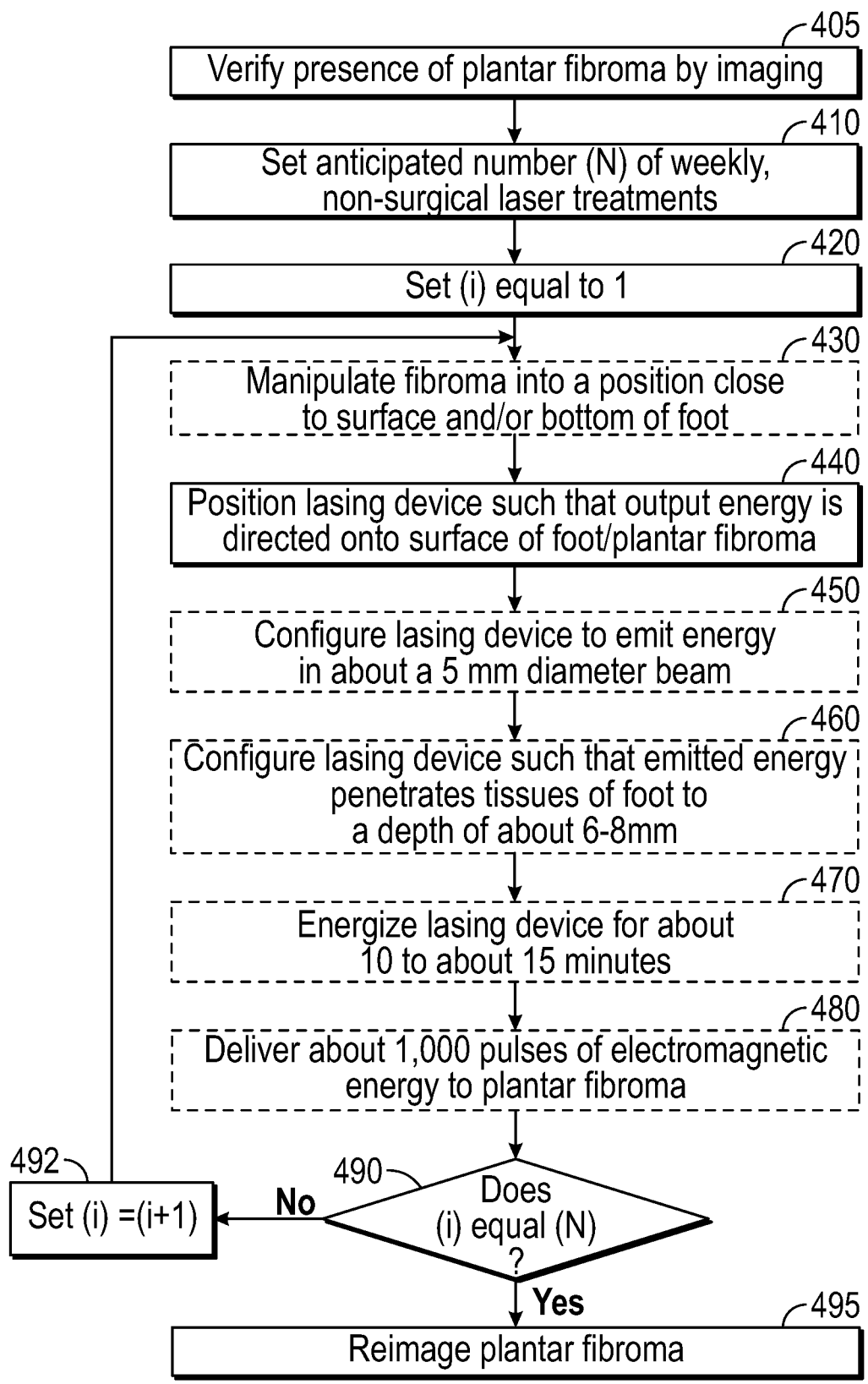
FIG. 4 is a flowchart summarizing the steps of Applicant's method for treating plantar fibroma.
Figure 5A:
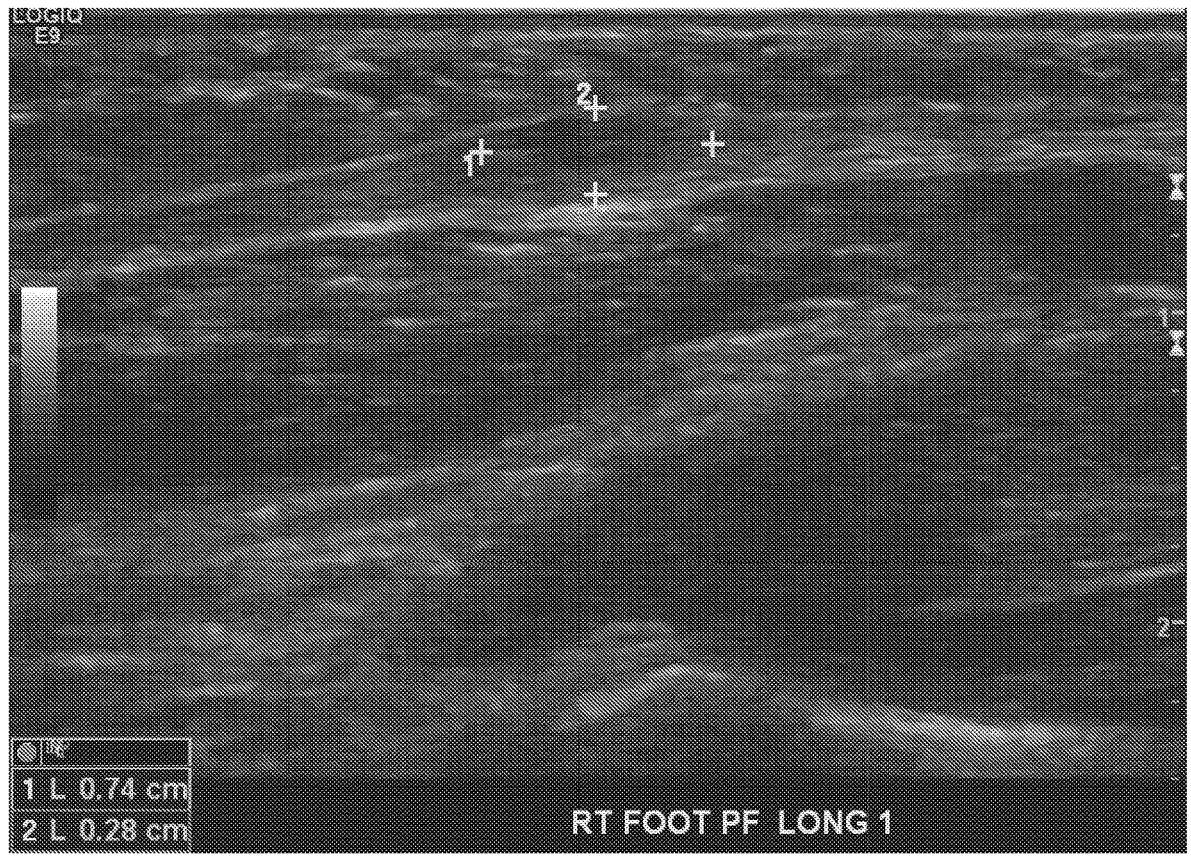
FIG. 5A is an ultrasound image showing a plantar fibroma before the laser treatment.
Figure 5B:
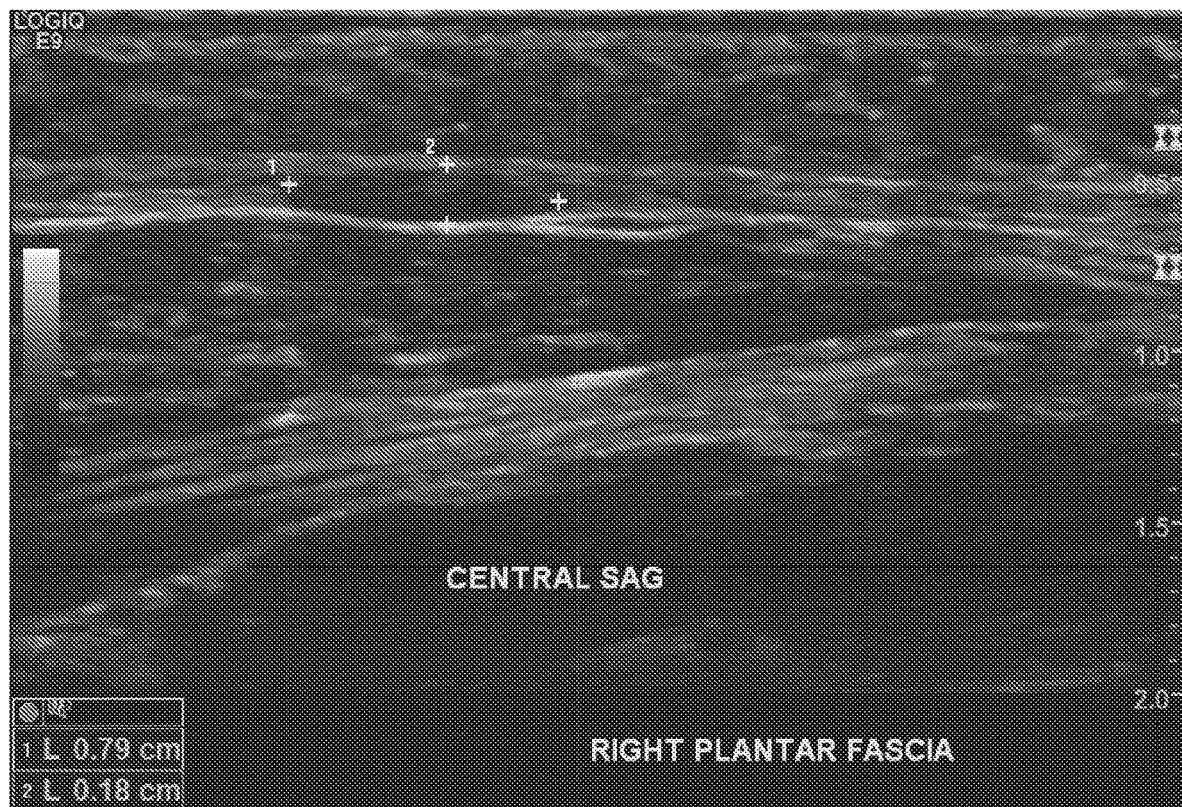
FIG. 5B is an ultrasound image showing the plantar fibroma that is reduced in size after the laser treatment.

FIG. 4 summarizes the steps of Applicant's method for treating plantar fibroma. Referring now to FIG. 4, in step 405 the method verifies the presence of a plantar fibroma using one or more medical imaging techniques. Such medical imaging techniques include, without limitation, magnetic resonance imaging ("MM") and/or ultrasound imaging.

In certain embodiments, the target area of the fibroma is identified using Applicant's "Dull Probe Technique," wherein that technique includes using a dull probe while patient is in the supine position, palpating the arches of the foot to elicit pain consistent with his/her chief complaint. A diagnostic ultrasound is also used to identify the specific location of the fibroma. The target area (including size, shape, and boarders of the plantar fibroma) is marked on the plantar surfaces and/or the arches of foot to guide laser treatment.

In step 410, and based upon the medical imaging of step 410, the method sets an anticipated number of weekly, non-surgical laser treatments. In step 420, the method sets a variable (i) to 1. In certain embodiments, the anticipated number of weekly, non-surgical laser treatments equals to 10.

In step 430, the method manipulates the verified plantar fibroma into a position adjacent to a surface and/or a bottom of the patient's foot. In step 440, the method positions a lasing device such that output power emitted by that lasing device is directed onto the surface of the patient's foot directly over the plantar fibroma.

In certain embodiments, step 430 further comprises applying a topical medication to the area of the foot directly over top of the plantar fibroma. Applicant's topical medication, which can be made in the form of cream, gel, ointment, and lotion, is made by a compounding pharmacy. The topical medication in the form of cream comprises Verapamil 15% by weight, Pentoxifylline 3% by weight, and Tranilast 1% by weight. In other embodiments, the topical medication in the form of lotion comprises Verapamil 15% by volume, Pentoxifylline 3% by volume, and Tranilast 1% by volume. The medication is applied just prior to the laser treatment and is allowed to absorb.

Applicant's topical medication is used to treat fibrotic conditions, like plantar fibromas, Dupuytren contracture, and scar tissues. Applicant has found that use of this topical medication assists treatment of the fibrosis around the plantar fascia when used with the Nd:YAG laser.

In certain embodiments, the lasing device of step 440 comprises a Nd:YAG laser.

In step 450, the method configures the lasing device of step 440 to emit electromagnetic energy in a beam comprising a about 5 mm spot size diameter. In step 460, the method configures the lasing device such that electromagnetic energy emitted by that lasing device penetrates tissues of the foot to a depth of between 6 mm and 8 mm. Applicant has demonstrated with magnetic resonance imaging that this tissue depth is sufficient to reach the candidate plantar fibromas. A sonography study has shown that most plantar fibromas (nodules) are located superficially in the plantar fascia.

In step 470, the method energizes the lasing device for between about 10 to about 15 minutes. In step 480, in certain embodiments, the method non-surgically delivers about 2,000 pulses of electromagnetic energy at 15 J/cm$^2$, 6 msec and 7 Hz to the plantar fibroma. Step 480 does not include cutting of the patient's skin. More specifically, step 480 does not include cutting the patient's skin disposed over or adjacent to the plantar fibroma. Step 480 does not include closure of a previously sustained wound.

In step 490, the method determines if (i) equals (N). If the method determines in step 490, that (i) does not equal (N), then the method transitions from step 490 to step 492 wherein the method increments (i) by 1, i.e. sets (i) equal to (i+1), The method then transitions from step 492 to step 430 and continues as described herein.

If the method determines in step 490, that (i) does equal (N), then the method transitions from step 490 to step 495 wherein the method reimages the plantar fibroma.

The following examples are presented to further illustrate to persons skilled in the art how to make and use the invention. These examples are not intended as a limitation, however, upon the scope of the invention.

Example 1

This Example 1 comprises an unsolicited testimonial from a patient of Applicant. "My Morton's Neuroma symptoms started a few years ago, beginning with bent toes and a tingling, burning sensation on the bottom of my right foot. Dr. Bocian treated me initially with cortisone injections, which worked well for about a year each. Then the symptoms intensified and I felt like I was walking on a marble. Over a few months' time, I was limping badly, causing pain in the left knee and leg. I started actually calculating how many steps I could avoid in daily activities."

In October, I saw Dr. Bocian and asked what we could do short of surgery so I could recover quality of life and normalcy of movement. He told me about his laser treatment and I began the course of 10 immediately. After treatment no. 2, 1 felt 95% better.

I feel privileged to have been in Dr. Bocian's care and offered his new application of laser technology for Morton's neuroma."

Example 2

History: 58-year-old female with bilateral feet Morton's neuroma status post laser therapy for follow-up.

Comparison: Ultrasound of the right and left feet from 02107/2014. Technique: Focused grayscale and power Doppler ultrasound examination of both feet with attention to the forefoot was performed for follow-up bilateral Morton's neuromas.

Right foot: Redemonstrated is a round hypoechoic lesion at the plantar aspect of the second intermetatarsal space between the second and 3rd metatarsal heads which has decreased in size and now measures 0.2×0.2×0.2 cm (AP× TR×CC), consistent with a Morton's neuroma. Redemonstrated is a small fluid-filled lesion at the plantar lateral aspect of the 3rd metatarsophalangeal joint, measuring 5 mm in length, which is not contiguous with the Morton's neuroma, and may represent a small adventitial bursa or a ganglion cyst. There is no additional soft tissue abnormality at the remaining intermetatarsal spaces.

Left foot: Redemonstrated is a round heterogeneously hypoechoic lesion at the plantar aspect of the second intermetatarsal space between the second and 3rd metatarsal heads which has decreased in size and now measures 0.3×0.2×0.1 cm (AP×TR×CC), consistent with a Morton's neuroma. Redemonstrated is an additional ill-defined hypoechoic region at the 3rd intermetatarsal space between the 3rd and 4th metatarsal heads which also has decreased in size and n w measures 0.1×0.1×0.1 cm, which may represent an additional small Morton's neuroma. There are no additional soft tissue abnormalities at the remaining intermetatarsal spaces.

Impression: Bilateral second intermetatarsal space Morton's neuromas and left 3rd intermetatarsal space Morton's neuroma which have decreased in size when compared to reference examination.

Example 3

Thirty (30) patients underwent a study evaluating the effect of a Nd:YAG laser in the non-surgical treatment of Morton's neuroma. Baseline diagnostic MRI and/or ultrasound exams were used to confirm the presence of a neuroma. A series of weekly laser treatments were given using Applicant's method. Following completion of the treatments, subjects returned for a follow-up MR and/or ultrasound study.

The results yielded an extremely high patient satisfaction rate. Follow-up comparison studies revealed a decrease in the size of the neuroma.

Of 42 patients undergoing Morton's neuroma evaluation by US, 21 underwent treatment of a total of 32 Morton' neuromas. Retrospective US review of the pre-treatment lesion showed heterogeneously, hypoechoic masses with well-defined borders with associated pain on transducer pressure in 97% (31/32). An associated bursa (3/28) was identified in a minority of cases. Following treatment the lesions remained heterogeneously hypoechoic but most demonstrated ill-defined borders (23/31) with significantly decreased or absent pain with transducer pressure (29/31). Statistical analysis revealed significant differences in appearance of pre and post-treatment lesion borders ($p<0.0001$) and pain with transducer pressure ($p<0.0001$), as well as the presence of an associated intermetarsal bursa ($p<0.05$), which resolved following treatment, but not size. Finally, all neuromas were determined to be better visualized on US compared to MRI.

Example 3 demonstrates that the use of a Nd:YAG laser in the treatment of Morton's neuroma comprises an excellent option with satisfaction rates being superior to previous treatments. This procedure eliminates surgical intervention along with its associated risks and complications. In addition, out of pocket expense for the patient is reduced. Moreover, there is no down time, and therefore, patients may continue to work and enjoy leisure activities such as golfing, cycling and tennis as tolerable throughout the series of treatments.

Example 4

History: 57-year-old male with left second inter space Morton's neuroma status post laser therapy. Comparison: Prior left toot ultrasound dated Nov. 10, 2014. Technique: Grayscale and Doppler ultrasound roots views of the left forefoot were obtained.

Findings: There is redemonstration of hypoechoic lesion within the second intermetatarsal space, measuring 0.4×0.4× 0.3 cm (AP×TR×CC), which is slightly decreased in size compared to prior study measuring 0.4×0.5×0.3 cm. There is no significant interval change in the echogenicity or echo texture of this lesion. There is no pain with transducer pressure, which is improved compared to prior study. There is no additional lesion within the remaining interspaces of tile left toot.

Impression: There is redemonstration of hypoechoic lesion within the second demonstrates slight interval decrease in size with no pain on transducer pressure, consistent with successful treatment.

Example 5

This Example 5 comprises an unsolicited testimonial from a patient of Applicant.

"I became a patient of Dr. Bocian and in April 2015 after being referred by my primary care provider. I had been living with pain from a large plantar fibroma on my right foot for 2 years. The pain had been increasing over the prior 6 months, which caused me to change my lifestyle to avoid jogging, standing for extended time and long hikes. Since February 205, I would awake with painful cramping of the right foot in greater toe and would need to spend several minutes stretching before I could walk comfortably.

I have had plantar fibroma surgically removed from my left foot twice in years prior to this occurrence in my right foot. Both times my only options were to live with it or surgically remove it. I didn't care for the long, painful and troublesome recovery from the surgery so I avoided going back to the doctor for this new fibroma. After Dr. Bocian explained the option of laser treatment versus surgery, I was still hesitant about the treatment but I did not want to repeat the surgery route of treatment again. So I decided to give laser treatment a try.

The first 3 laser treatments were uncomfortable at times but Natasha (laser technologist) was very quick and skillful at easing the pain. With each further treatment, I noticed that the morning cramping and pain was disappearing and the nodules were getting softer and smaller. By the end of the treatment plan, I was not having any pain or discomfort in my right foot. The only time I had discomfort was after walking barefoot and stepped on a rock right on the fibroma. It did hurt for a few moments.

Since finishing the treatment in July 2015 I've not had any pain or cramping of the right foot. My wife and I have gone on long and hard hikes with no discomfort to me. I still have the nodules, but they are softer and smaller. I'm very happy that I took this path for treatment. I knew from the outset that Dr. Bocian could not promise the fibroma would go away but the pain and discomfort did. Thank you Dr. Bocian and Natasha."

Example 6

This Example 6 comprises an unsolicited testimonial from a patient of Applicant.

"I told Dr. Bocian I was experiencing pain on the arch of my left foot. He sent me for a diagnostic ultrasound and explained I had Plantar Fibromatosis. He suggested I try a fairly new laser treatment. I elected to follow his advice and get the laser treatment rather than having surgery to remove the fibromas.

My foot was so sensitive Dr. Bocian could barely touch it without me jumping out of my chair. Honestly, I was a little skeptical. The first treatment was awful and left me in tears. I was not looking forward to the remaining treatments but knew I had to go through with them due to the pain I was experiencing and the affect it was having on my quality of life.

With each treatment, my foot was getting better and there was less and less pain. By the ninth treatment I was 100% better, the laser worked wonderfully and I couldn't be happier. I'm so glad I continued the treatment each week. Jam back to dancing and getting my quality of life back.

When I went back to get my follow-up diagnostic ultrasound at University of Arizona Medical Center, the tech remembered me and told me she couldn't believe the difference. She said when she did my first ultrasound, I would pull my foot away and now she was able to press on my foot and there was no pain.

I want to thank Dr. Bocian and Natasha for being so patient with me. My treatments took longer than normal due to the sensitivity of my foot and they had to keep stopping. I would recommend this treatment to anyone experiencing Plantar Fibromatosis and to not get discouraged after the first treatment! It gets better! Thank you again!"

Example 7

This Example 7 comprises an unsolicited testimonial from a patient of Applicant.

"I'm a nurse who works long 12 hour shifts. I began having pain in the arch and heel of my right foot a year and a half ago. As time went on, the pain got increasingly worse. The pain began affecting my daily life. I had spent hundreds of dollars on shoes, pain creams, and over the counter orthotics with no help. I finally went to see Dr. Bocian and was given all options from orthotics, laser, and surgery. Surgery was not an option for me due to cost and down time. I opted for the custom orthotics and laser. The price was much more affordable and no down time! I will admit that I was a little skeptical about the laser at first, but I trusted in Dr. Bocian that this will work. By the time my treatment coarse came to an end, I was amazed how well the laser worked! I am now back to doing the things in life that I had stopped doing because of the foot pain. I owe Dr. Bocian and his laser technician Natasha a huge thank you!"

Example 8

This Example 8 comprises an unsolicited testimonial from a patient of Applicant.

"I am extremely happy with my laser treatment given by Dr. Bocian and Natasha, his assistant, for my painful plantar fibroma. They are both very skilled in using the laser and it is a very good option for this painful condition.

It took away the discomfort and caused it to shrink away to almost nothing. I am back to walking and jogging and was able to do 6.6 miles with no problem. Thanks again! I highly recommend Dr. Bocian's laser treatment for Plantar Fibroma."

Example 9

This Example 9 comprises an unsolicited testimonial from a patient of Applicant.

"Last July I limped into your office with a lump on the sole of my foot and in severe pain. You diagnosed the lump as plantar fibroma. I had a trip to Yellowstone planned in 4 weeks, so you immediately started me on a series of laser treatments. The fibroma improved sufficiently in 4 weeks, so that I was able to enjoy my trip.

Today, after 13 laser treatments, I am back to all my normal activities which includes walking for exercise. I would definitely recommend laser treatment for anyone suffering from plantar fibroma."

While the preferred embodiments of the present invention have been illustrated in detail, it should be apparent that modifications and adaptations to those embodiments may occur to one skilled in the art without departing from the scope of the present invention.

The invention claimed is:

1. A method for treating a fibrous mass comprised of a plantar fibroma in a human foot, the method comprising:
   identifying a location of the fibrous mass in the foot using a medical imaging technique;
   determining a size of the fibrous mass located;
   non-surgically delivering electromagnetic energy from a lasing device comprising a Nd:Yag laser to the located fibrous mass during a treatment of a plurality of treatments of the foot, each treatment including:
   applying a topical medication directly on a skin surface at a location where each treatment of the located fibrous mass is being administered, wherein the topical medication comprises two or more of verapamil, pentoxifylline, and/or tranilast;
   directing a beam of the laser over a 5 mm diameter spot on a skin surface of the foot such that the beam irradiates the location of the fibrous mass;
   adjusting a power of the lasing device up to 15 $J/cm^2$ such that the electromagnetic energy penetrates tissues to a depth of about 6 mm to about 8 mm;
   delivering at least 2,000 pulses of the laser to the location, per treatment; and
   directing the beam onto the location to irradiate the fibrous mass for 10 minutes;
   performing 10 of the treatments, and thereby reducing a size of the fibrous mass and softening the fibrous mass to an extent such that the patient is relieved of disability resulting from the plantar fibroma beyond mere reduction in a pain level-associated with the fibrous mass.

2. The method of claim 1 wherein using the medical imaging techniques further comprises using magnetic resonance imaging.

3. The method of claim 1 wherein using the medical imaging techniques further comprises using ultrasound imaging.

4. The method of claim 1, further comprising:
   directing the beam onto the location for 15 minutes.

5. The method of claim 1, wherein the topical medication comprises verapamil, pentoxifylline, and tranilast.

6. The method of claim 1, wherein the topical medication comprises about 15% verapamil by weight or volume, about 3% pentoxifylline by weight or volume, and/or about 1% tranilast by weight or volume.

7. The method of claim 1, wherein the topical medication comprises about 15% verapamil by weight or volume, about 3% pentoxifylline by weight or volume, and about 1% tranilast by weight or volume.

8. A method for treating a fibrous mass comprised of a plantar fibroma in a human foot, the method comprising:
 identifying a location of the fibrous mass in the foot;
 non-surgically delivering electromagnetic energy from a lasing device comprising a Nd:Yag laser to the located fibrous mass during a treatment of a plurality of treatments of the foot, each treatment including:
  directing a beam of the laser having a frequency of 7 Hz over a 5 mm diameter spot on a skin surface of the foot such that the beam irradiates the location of the fibrous mass;
  adjusting a power of the lasing device such that the electromagnetic energy penetrates tissue of the foot to a depth of 6 mm to 8 mm and has an energy of up to 15 $Jcm^2$ across an area of the skin surface impinged by the beam during irradiation of the fibrous mass;
  delivering 1,000 pulses of the laser to the location, per treatment;
  wherein each of the pulses is applied for a time period of 6 milliseconds;
  directing the beam onto the location to irradiate the fibrous mass for 10 minutes;
  performing 10 of the treatments, and thereby reducing a size of the fibrous mass and softening the fibrous mass to an extent such that the patient is relieved of disability resulting from the plantar fibroma beyond mere reduction in a pain level-associated with the fibrous mass.

9. The method of claim 8 wherein using the medical imaging techniques further comprises using magnetic resonance imaging.

10. The method of claim 8 wherein using the medical imaging techniques further comprises using ultrasound imaging.

11. The method of claim 8 wherein each of the plurality of treatments further include:
 applying a topical medication directly on a skin surface at a location where each treatment of the located fibrous mass is being administered, wherein the topical medication comprises two or more of verapamil, pentoxifylline, and/or tranilast.

12. The method of claim 11, wherein the topical medication comprises verapamil, pentoxifylline, and tranilast.

13. The method of claim 11, wherein the topical medication comprises about 15% verapamil by weight or volume, about 3% pentoxifylline by weight or volume, and/or about 1% tranilast by weight or volume.

14. The method of claim 11, wherein the topical medication comprises about 15% verapamil by weight or volume, about 3% pentoxifylline by weight or volume, and about 1% tranilast by weight or volume.

15. A method for treating a fibrous mass comprised of a plantar fibroma in a human foot, the method comprising:
 identifying a location of the fibrous mass in the foot using a medical imaging technique;
 determining a size of the fibrous mass located;
 non-surgically delivering electromagnetic energy from a lasing device comprising a Nd:Yag laser to the located fibrous mass during a treatment of a plurality of treatments of the foot, each treatment including:
  applying a topical medication directly on a skin surface at a location where each treatment of the located fibrous mass is being administered, wherein the topical medication comprises two or more of verapamil, pentoxifylline, and/or tranilast;
  directing a beam of the laser having a frequency of 7 Hz over a spot on a skin surface of the foot such that the beam irradiates the location of the fibrous mass;
  adjusting a power of the lasing device up to 15 $J/cm^2$ such that the electromagnetic energy penetrates tissues to a depth of about 6 mm to about 8 mm;
  delivering at least 2,000 pulses of the laser to the location, per treatment; and
  directing the beam onto the location to irradiate the fibrous mass for 10 minutes;
  performing 10 of the treatments, and thereby reducing a size of the fibrous mass and softening the fibrous mass to an extent such that the patient is relieved of disability resulting from the plantar fibroma beyond mere reduction in a pain level-associated with the fibrous mass.

16. The method of claim 15 wherein using the medical imaging techniques further comprises using magnetic resonance imaging.

17. The method of claim 15 wherein using the medical imaging techniques further comprises using ultrasound imaging.

18. The method of claim 15, wherein the topical medication comprises verapamil, pentoxifylline, and tranilast.

19. The method of claim 15, wherein the topical medication comprises about 15% verapamil by weight or volume, about 3% pentoxifylline by weight or volume, and/or about 1% tranilast by weight or volume.

20. The method of claim 15, wherein the topical medication comprises about 15% verapamil by weight or volume, about 3% pentoxifylline by weight or volume, and about 1% tranilast by weight or volume.

21. The method as in any one of claims 1, 2, 3, 4, 5, 6, 7, 9, 10 or 8-20 wherein, as a result of administering the plurality of the treatments, size of the fibrous mass' lesion border is reduced at least 33% in measure, as determined via comparison of a first image taken via the medical imaging technique before the plurality of treatments are administered and a second image taken via the medical imaging technique after the plurality of treatments are administered.

22. The method of claim as in any one of claims 1, 2, 3, 4, 5, 6, 7, 9, 10 or 8-20 wherein, as a result of administering the plurality of the treatments, the size of the fibrous masses is reduced at least 33%.

23. The method of claim 22 wherein, as a result of administering the plurality of the treatments, size of the fibrous mass' lesion border is reduced at least 33% in measure, as determined via comparison of a first image taken via the medical imaging technique before the plurality of treatments are administered and a second image taken via the medical imaging technique after the plurality of treatments are administered.

24. The method as in any one of claims 1, 2, 3, 4, 5, 6, 7 or 15-20, wherein the pulses have a period of 6 msec.

* * * * *